United States Patent
Woods et al.

(10) Patent No.: US 10,504,623 B2
(45) Date of Patent: Dec. 10, 2019

(54) ORTHOPAEDIC INSTRUMENT SYSTEM AND METHOD FOR DETERMINING DURATION OF USE OF AN ORTHOPAEDIC INSTRUMENT

(71) Applicant: DePuy Synthes Products, Inc., Raynham, MA (US)

(72) Inventors: Sherrod A. Woods, Fort Wayne, IN (US); Cassidy A. Topel, Warsaw, IN (US); Omari Gardner, Warsaw, IN (US)

(73) Assignee: DePuy Synthes Products, Inc., Raynham, MA (US)

( * ) Notice: Subject to any disclaimer, the term of this patent is extended or adjusted under 35 U.S.C. 154(b) by 161 days.

(21) Appl. No.: 15/856,336

(22) Filed: Dec. 28, 2017

(65) Prior Publication Data

US 2019/0206548 A1    Jul. 4, 2019

(51) Int. Cl.
| | |
|---|---|
| *A61B 90/96* | (2016.01) |
| *G16H 40/20* | (2018.01) |
| *A61B 50/33* | (2016.01) |
| *G06K 7/10* | (2006.01) |
| *G07C 1/10* | (2006.01) |
| *A61B 90/98* | (2016.01) |
| *A61B 90/00* | (2016.01) |
| *A61B 50/00* | (2016.01) |

(52) U.S. Cl.
CPC ............. *G16H 40/20* (2018.01); *A61B 50/33* (2016.02); *A61B 90/98* (2016.02); *G06K 7/10762* (2013.01); *G07C 1/10* (2013.01); *A61B 90/96* (2016.02); *A61B 2050/0056* (2016.02); *A61B 2090/0803* (2016.02)

(58) Field of Classification Search
CPC ................................ A61B 50/33; A61B 90/96
USPC .................................................. 235/375, 377
See application file for complete search history.

(56) References Cited

U.S. PATENT DOCUMENTS

| | | | |
|---|---|---|---|
| 6,366,206 B1 | 4/2002 | Ishikawa et al. | |
| 7,118,029 B2 | 10/2006 | Nycz et al. | |
| 7,362,228 B2 | 4/2008 | Nycz et al. | |
| 7,644,016 B2 | 1/2010 | Nycz et al. | |
| 9,937,010 B2 * | 4/2018 | Weinert | G06K 7/10366 |
| 10,321,972 B2 * | 6/2019 | Weinert | G06K 7/10366 |
| 2002/0143320 A1 | 10/2002 | Levin | |
| 2003/0196837 A1 | 10/2003 | Ballard | |
| 2004/0008123 A1 | 1/2004 | Carrender et al. | |
| 2004/0220602 A1 | 11/2004 | Deng et al. | |
| 2005/0012617 A1 | 1/2005 | DiSilvestro et al. | |
| 2006/0043177 A1 * | 3/2006 | Nycz | G06Q 10/087 235/385 |
| 2006/0043179 A1 | 3/2006 | Nycz et al. | |
| 2006/0244593 A1 | 11/2006 | Nycz et al. | |

(Continued)

FOREIGN PATENT DOCUMENTS

WO    2014152238 A2    9/2014

*Primary Examiner* — Paultep Savusdiphol
(74) *Attorney, Agent, or Firm* — Barnes & Thornburg LLP

(57) ABSTRACT

An orthopaedic surgical instrument system includes an orthopaedic surgical instrument tray and an orthopaedic surgical instrument that is configured to be positioned in the instrument tray. The orthopaedic surgical instrument system also includes a machine-readable optical label that is associated with the instrument. The system is configured to determine a duration of use of the instrument based on whether the machine-readable optical label is detected.

18 Claims, 5 Drawing Sheets

(56) References Cited

U.S. PATENT DOCUMENTS

| | | | |
|---|---|---|---|
| 2008/0150722 A1 | 6/2008 | Jackson | |
| 2009/0272806 A1* | 11/2009 | Kemp | B23K 26/03 |
| | | | 235/462.1 |
| 2009/0317002 A1* | 12/2009 | Dein | A61B 50/362 |
| | | | 382/224 |
| 2011/0036738 A1* | 2/2011 | Hiltl | B65F 1/0046 |
| | | | 206/459.1 |
| 2014/0152238 A1 | 6/2014 | Racenet et al. | |
| 2015/0190202 A1* | 7/2015 | Weinert | G06K 7/10366 |
| | | | 340/5.8 |
| 2016/0066915 A1* | 3/2016 | Baber | A61B 17/072 |
| | | | 227/178.1 |
| 2017/0363554 A1 | 12/2017 | Freeman et al. | |
| 2018/0082480 A1* | 3/2018 | White | A61B 50/33 |
| 2018/0204323 A1* | 7/2018 | Sayani | G06Q 10/087 |
| 2018/0214243 A1* | 8/2018 | Weinert | G06K 7/10366 |
| 2019/0090954 A1* | 3/2019 | Kotian | A61B 34/20 |

* cited by examiner the instrument when the instrument is positioned in the instrument tray. The memory device includes a plurality of instructions that, when read by the processor, cause the

ORTHOPAEDIC INSTRUMENT SYSTEM AND METHOD FOR DETERMINING DURATION OF USE OF AN ORTHOPAEDIC INSTRUMENT

TECHNICAL FIELD

The present disclosure relates generally to orthopaedic instruments for use in the performance of an orthopaedic joint replacement procedure, and, more particularly, to an instrument system for an orthopaedic procedure using a plurality of orthopaedic instruments.

BACKGROUND

Joint arthroplasty is a well-known surgical procedure by which a diseased and/or damaged natural joint is replaced by a prosthetic joint. For example, in a total knee arthroplasty surgical procedure, a patient's natural knee joint is partially or totally replaced by a prosthetic knee joint or knee prosthesis. A typical knee prosthesis includes multiple prosthetic components, including a tibial tray, a femoral component, and a polymer insert or bearing positioned between the tibial tray and the femoral component. The tibial tray generally includes a plate having a stem extending distally therefrom, and the femoral component generally includes a pair of spaced apart condylar elements, which include surfaces that articulate with corresponding surfaces of the polymer bearing. The stem of the tibial tray is configured to be implanted in a surgically-prepared medullary canal of the patient's tibia, and the femoral component is configured to be coupled to a surgically-prepared distal end of a patient's femur.

During any orthopaedic surgery, the orthopaedic surgeon typically uses a variety of different orthopaedic surgical instruments such as, for example, broaches, cutting blocks, reamers, drill guides, and other surgical instruments to prepare the patient's bones to receive the knee prosthesis. The instruments are generally organized within an instrument tray that is accessible to the surgeon throughout the procedure. During the procedure, the surgeon or other user removes various instruments from the tray for use in the procedure.

SUMMARY

According to one aspect of the disclosed embodiments, an orthopaedic surgical instrument system includes an orthopaedic surgical instrument tray and an orthopaedic surgical instrument that is configured to be positioned in the instrument tray. The orthopaedic surgical instrument system also includes a machine-readable optical label that is associated with the instrument. The system is configured to determine a duration of use of the instrument based on whether the machine-readable optical label is detected.

According to another aspect of the disclosed embodiments, an orthopaedic surgical instrument system includes an orthopaedic surgical instrument tray. An orthopaedic surgical instrument is configured to be positioned in the instrument tray. A machine-readable optical label is positioned in the instrument tray and associated with the instrument. An imaging device is operable to read the optical label. An electronic controller includes a processor operable to receive output signals from the imaging device and a memory device. The optical label is sized to be covered by the instrument when the instrument is positioned in the instrument tray. The memory device includes a plurality of instructions that, when read by the processor, cause the processor to detect, based on the output signals from the imaging device, the optical label when the instrument is removed from the instrument tray. The optical label is interpreted to identify the instrument and record a first time indicating that the instrument is removed from the instrument tray. A second time is record, based on the output signals from the imaging device, when the optical label is no longer detected. The first time is compared to the second time to determine a duration of use of the instrument.

In some embodiments, the system may have a second orthopaedic surgical instrument, and a second machine-readable optical label associated with the second orthopaedic surgical instrument. The memory device may have a plurality of instructions that, when read by the processor, cause the processor to detect, based on the output signals from the imaging device, the second optical label when the second instrument is removed from the instrument tray. The second optical label may be interpreted to identify the second instrument. A second duration of use of the second instrument may be determined.

In some embodiments, a motion sensor may detect movement of the instrument. The processor may be operable to receive output signals from the motion sensor. The memory device may have a plurality of instructions that, when read by the processor, cause the processor to detect, based on the output signals from the motion sensor, movement of the instrument. The output signals may be retrieved from the imaging device when movement of the instrument is detected.

In some embodiments, a database may store data related to the duration of use.

According to yet another aspect of the disclosed embodiments, an orthopaedic surgical instrument system includes an orthopaedic surgical instrument. A machine-readable optical label is associated with the instrument. An imaging device is operable to read the optical label. An electronic controller includes a processor operable to receive output signals from the imaging device and a memory device. The memory device includes a plurality of instructions that, when read by the processor, cause the processor detect, based on the output signals from the imaging device, the optical label when the instrument is in use. The optical label is interpreted to identify the instrument and record a first time indicating that the instrument is in use. A second time is recorded, based on the output signals from the imaging device, when the instrument is no longer in use. The first time is compared to the second time to determine a duration of use of the instrument.

In some embodiments, the system may have an instrument tray having a chamber to store the instrument. The optical label may be positioned on a bottom wall of the chamber. The instrument tray may have a body and lid hinged to the body. The chamber may be formed in the body. The imaging device may be positioned in the lid. The lid may be configured to angle relative to the body so that the imaging device is angled toward the optical label. A sleeve may be attached to the lid and configured to receive the imaging device.

In some embodiments, an arm may be configured to hold the imaging device over the optical label.

In some embodiments, a motion sensor may detect movement of the instrument. The processor may be operable to receive output signals from the motion sensor. The memory device may have a plurality of instructions that, when read by the processor, cause the processor to detect, based on the output signals from the motion sensor, movement the instrument. The output signals may be retrieved from the imaging device when movement of the instrument is detected.

According to a further aspect of the disclosed embodiments, a method of determining a duration of use of an orthopaedic surgical instrument includes detecting a machine-readable optical label associated with an orthopaedic surgical instrument when the instrument is in use. The method also includes interpreting the optical label to identify the instrument when the instrument is in use. The method also includes determining when the optical label is no longer detected. The method also includes determining a duration of use of the instrument based on when the optical label was detected.

In some embodiments, when the instrument is not in use the instrument may be positioned over the optical label such that the optical label is unreadable. The method may require detecting the optical label when the optical label becomes readable as the instrument is removed from the optical label. The method may require continuing to monitor the optical label when the optical label is readable. The method may require determining that the optical label is no longer detected when the instrument is positioned back over the optical label after use and the optical label becomes unreadable.

In some embodiments, the method may require detecting a second optical label associated with a second instrument when the second instrument is in use. The method may require interpreting the second optical label to identify the second instrument when the second instrument is in use. The method may require determining a duration of use of the second instrument based on when the second optical label was detected.

In some embodiments, the optical label may be positioned in an instrument tray. The method may require detecting the optical label when the instrument is removed from the instrument tray. In some embodiments, the optical label in positioned on a surgical drape. The method may require detecting the optical label when the instrument is removed from the surgical drape.

BRIEF DESCRIPTION OF THE DRAWINGS

The detailed description particularly refers to the following figures, in which.

DETAILED DESCRIPTION

Figure 1:
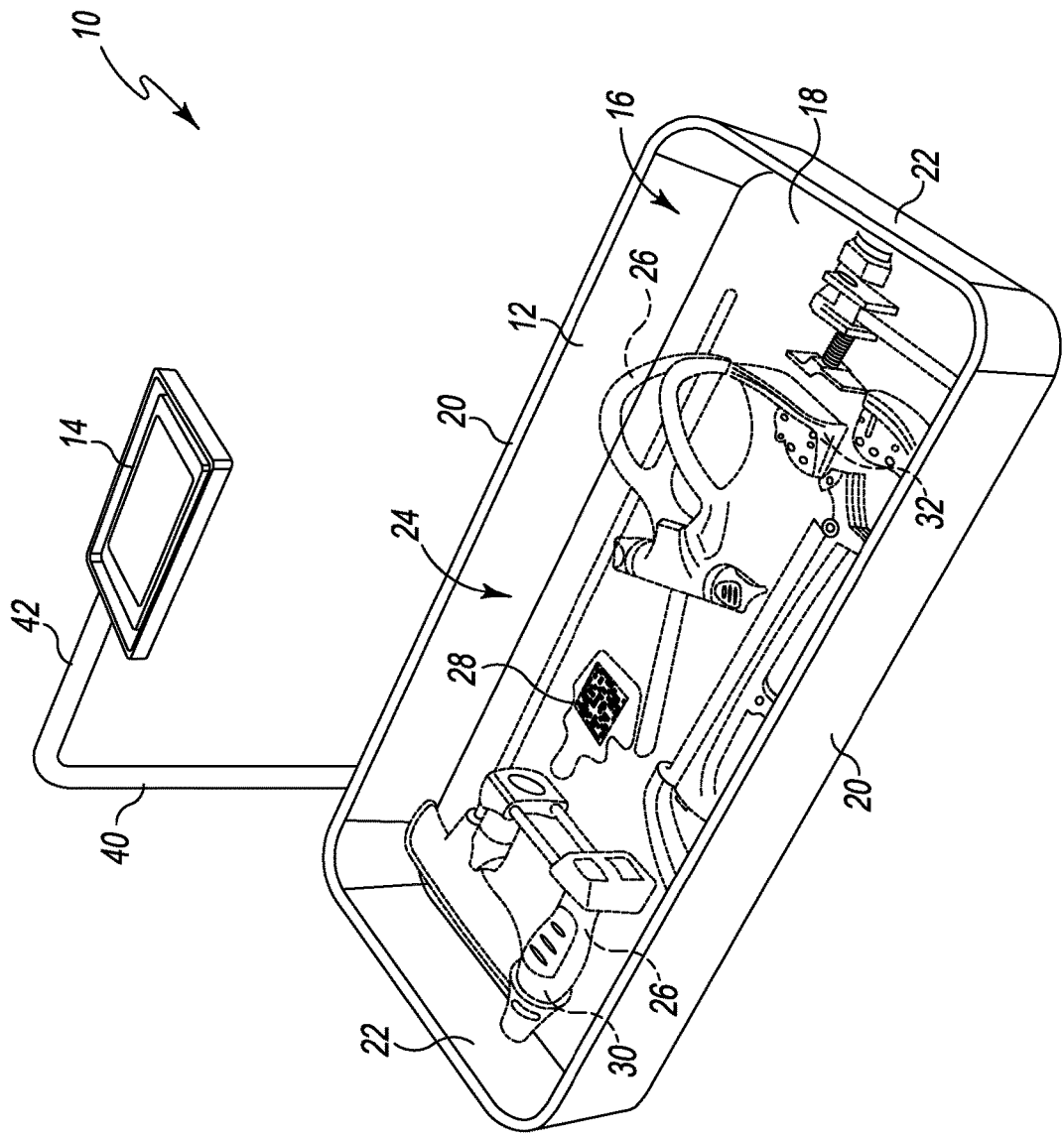
FIG. 1 is a top perspective view of an orthopaedic surgical instrument system.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout the specification in reference to the orthopaedic implants and orthopaedic surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise.

Referring now to FIG. 1, an orthopaedic surgical instrument system 10 includes an instrument tray 12 and a computing device 14. As discussed in more detail below, during an orthopaedic surgical procedure, the computing device 14 monitors the instrument tray 12 to determine which instruments are in use and a duration of time that each instrument is used. Knowledge of which instruments the surgeon typically uses in a procedure allows the surgeon to more selectively choose instruments for future procedures. Such data is also usable by a hospital when purchasing additional instruments.

Figure 2:
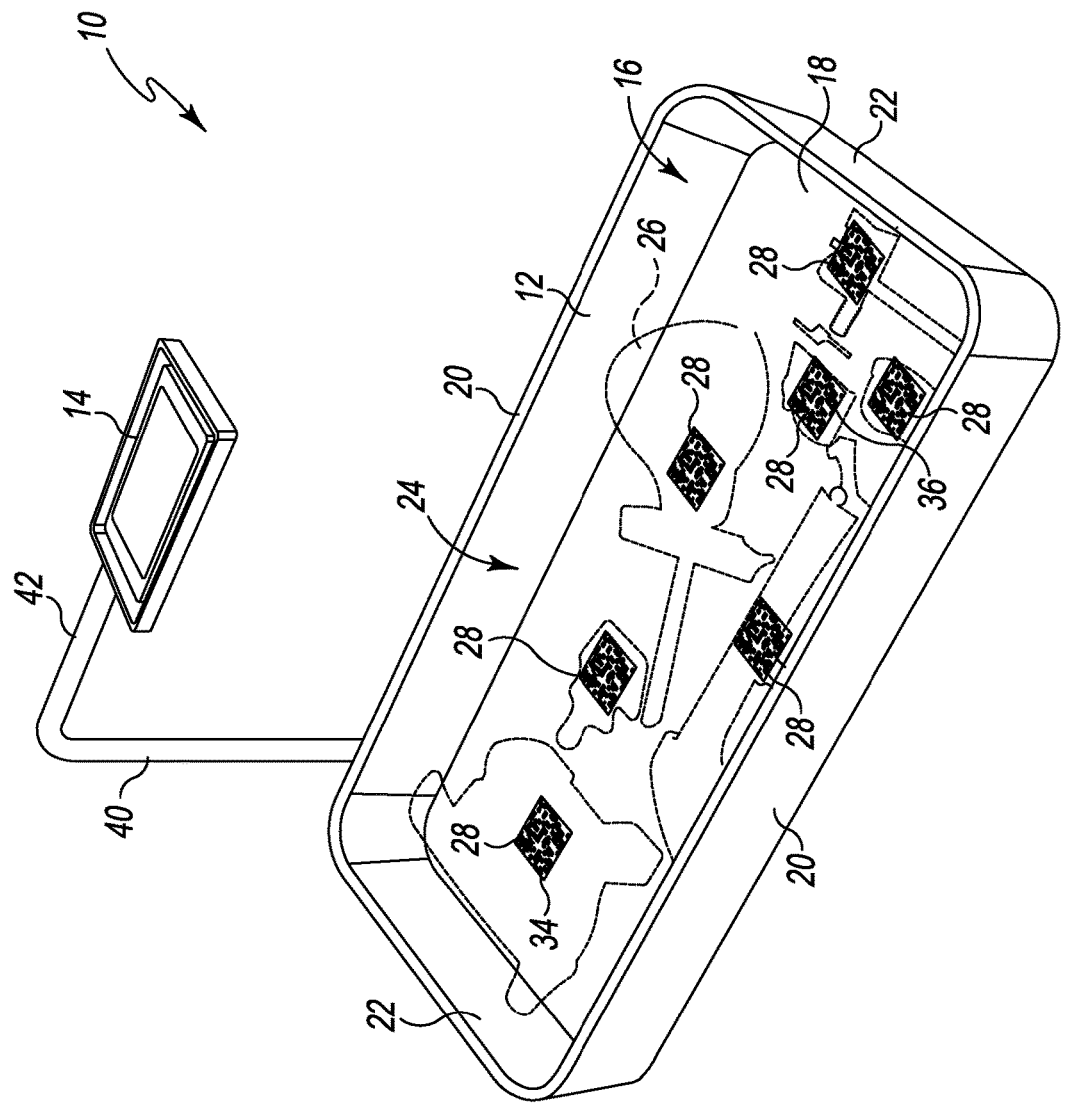
FIG. 2 is a top perspective view similar to FIG. 1 showing a plurality of orthopaedic surgical instruments removed from an instrument tray of the orthopaedic surgical instrument system.

The instrument tray 12 includes a body 16 having a bottom wall 18 and a pair of spaced apart longitudinal walls 20 extending upwardly from the bottom wall 18. A pair of spaced apart end walls 22 extends upwardly from the bottom wall 18 between the longitudinal walls 20. The bottom wall 18, the longitudinal walls 20, and the end walls 22 cooperate to define a storage chamber 24 that houses a plurality of orthopaedic surgical instruments 26. A plurality of unique machine-readable optical labels 28 is positioned on the bottom wall 18, as illustrated in FIG. 2. The optical labels 28 are barcodes, e.g. QR® codes. Each of the plurality of instruments 26 is positioned over an associated optical label 28. By way of example, the instruments 26 include a resection guide 30 and a cutting guide 32. The resection guide 30 is positioned over an optical label 34 (shown in FIG. 2) that is unique to the resection guide 30, and the cutting guide 32 is positioned over an optical label 36 (shown in FIG. 2) that is unique to the cutting guide 32. When the instrument 26 is positioned over the respective optical label 28, the optical label 28 is not within the view of the imaging device 44, as illustrated in FIG. 1, because the optical label 28 is sized to be covered by the instrument 26.

The orthopaedic surgical instrument system 10 includes a stand 40 that has an arm 42 to position the computing device 14 over the instrument tray 12. The stand 40 is coupled to the instrument tray 12. In some embodiments, the stand 40 may be a separate component that is positioned next to the instrument tray 12. As described in more detail below, the computing device 14 is positioned over the instrument tray 12 such that the optical labels 28 are within a field of view of an imaging device 44, e.g. a camera (described in more detail in FIG. 3), of the computing device 14. In such a configuration, the optical label 28 is not readable by the computing device 14. When the instruments 26 are removed from the instrument tray 12, as illustrated in FIG. 2, the optical labels 28 are within the field of view of the imaging device 44 and, therefore, readable by the computing device 14. Only a single instrument 26 need be removed from the surgical tray 12 for the associated optical label 28 to be readable. Any number of optical labels 28 may be readable at a given time. If more than one instrument 26 is removed from the instrument tray 12, the optical label 28 associated with each instrument 26 removed becomes visible and readable by the computing device 14.

Figure 3:
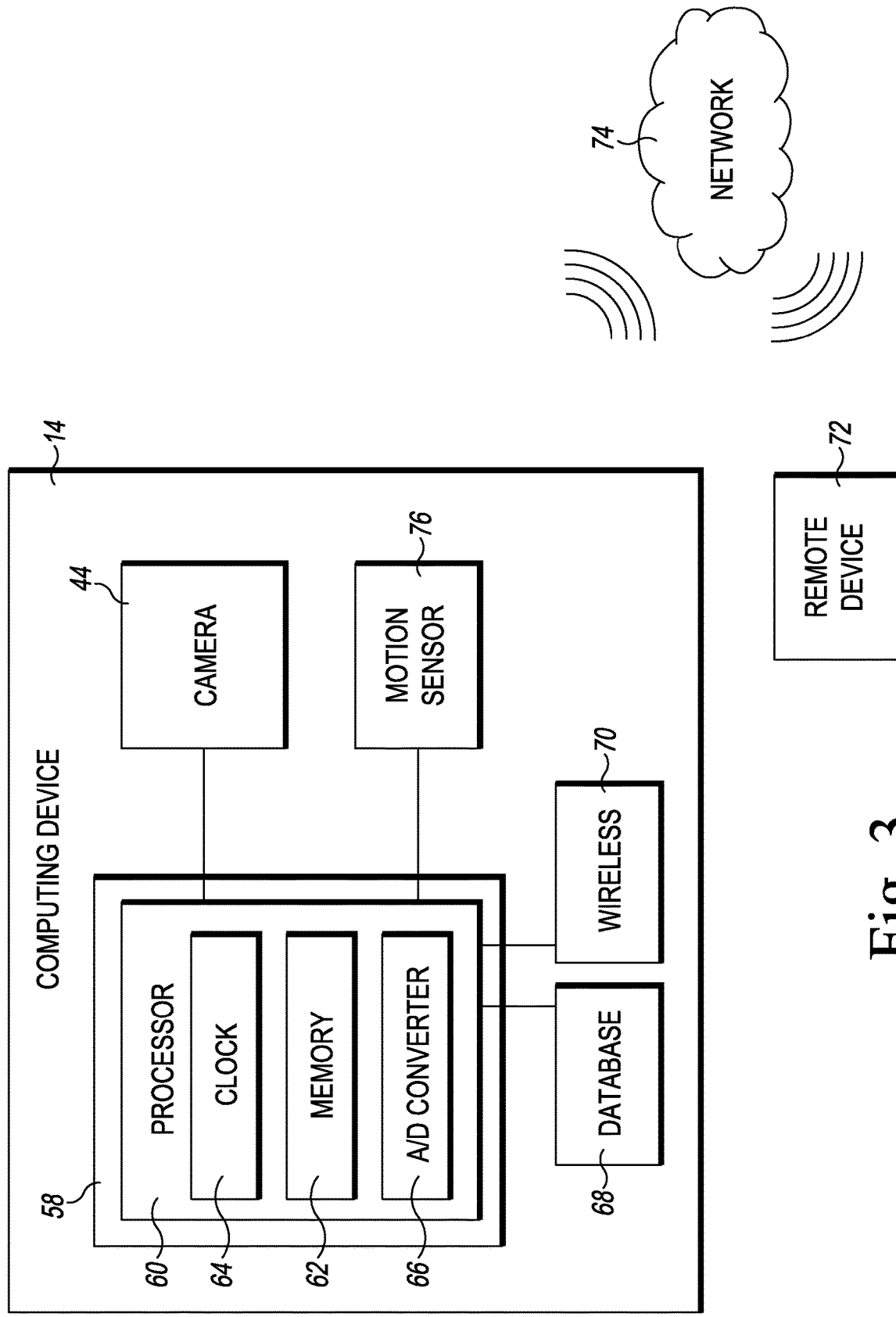
FIG. 3 is a schematic view of a computing device of the orthopaedic surgical instrument system of FIG. 1.

Referring to FIG. 3 the computing device 14 may be any device capable of processing data as described below. In some embodiments, the computing device 14 is a mobile device, e.g. a smart phone or tablet. The computing device 14 illustratively includes an electronic controller 58 having a processor 60, a memory 62, a clock 64, and an analog-to-digital converter 66. The processor 60 may be embodied as any type of processor capable of performing the functions described herein. The processor 60 may be embodied as a dual-core processor, a multi-core or multi-threaded processor, digital signal processor, microcontroller, or other processor or processing/controlling circuit with multiple processor cores or other independent processing units. The memory 62 may be embodied as any type of volatile or non-volatile memory or data storage capable of performing the functions described herein. In operation, the memory 62 may store various data and software used during operation of the computing device 14 such as operating systems, applications, programs, libraries, and drivers. The memory 62 includes a plurality of instructions that, when read by the processor, cause the processor to perform the functions described herein. A data storage device 68 is provided that may be embodied as any type of device or devices configured for short-term or long-term storage of data such as, for example, memory devices and circuits, memory cards, hard disk drives, solid-state drives, or other data storage devices. A wireless transceiver 70 of the computing device 14 may be embodied as any communication circuit, device, or collection thereof, capable of enabling wireless communications between the computing device 14 and other remote devices 72 over a network 74. The wireless transceiver 70 may be configured to use any one or more communication technology and associated protocols (e.g., Wi-Fi®, Bluetooth®, WiMAX, etc.) to effect such communication.

The imaging device 44 is in communication with the electronic controller 58 such that output signals from the imaging device 44 are transmitted to the processor 60. A motion sensor 76 is in communication with the electronic controller 58 such that output signals from the motion sensor 76 are transmitted to the processor 60. The motion sensor 76 is configured to detect movement of an instrument 26 within the instrument tray 12, e.g. removal of an instrument 26, and send output signals to the processor 60 instructing the processor to activate the imaging device 44. In some embodiments, the computing device 14 may be operated with the motion sensor 76 turned off. Alternatively, the computing device 14 may not include a motion sensor 76. In such embodiments, the imaging device 44 continually operates during the procedure and is not activated and deactivated throughout the procedure.

Figure 4:
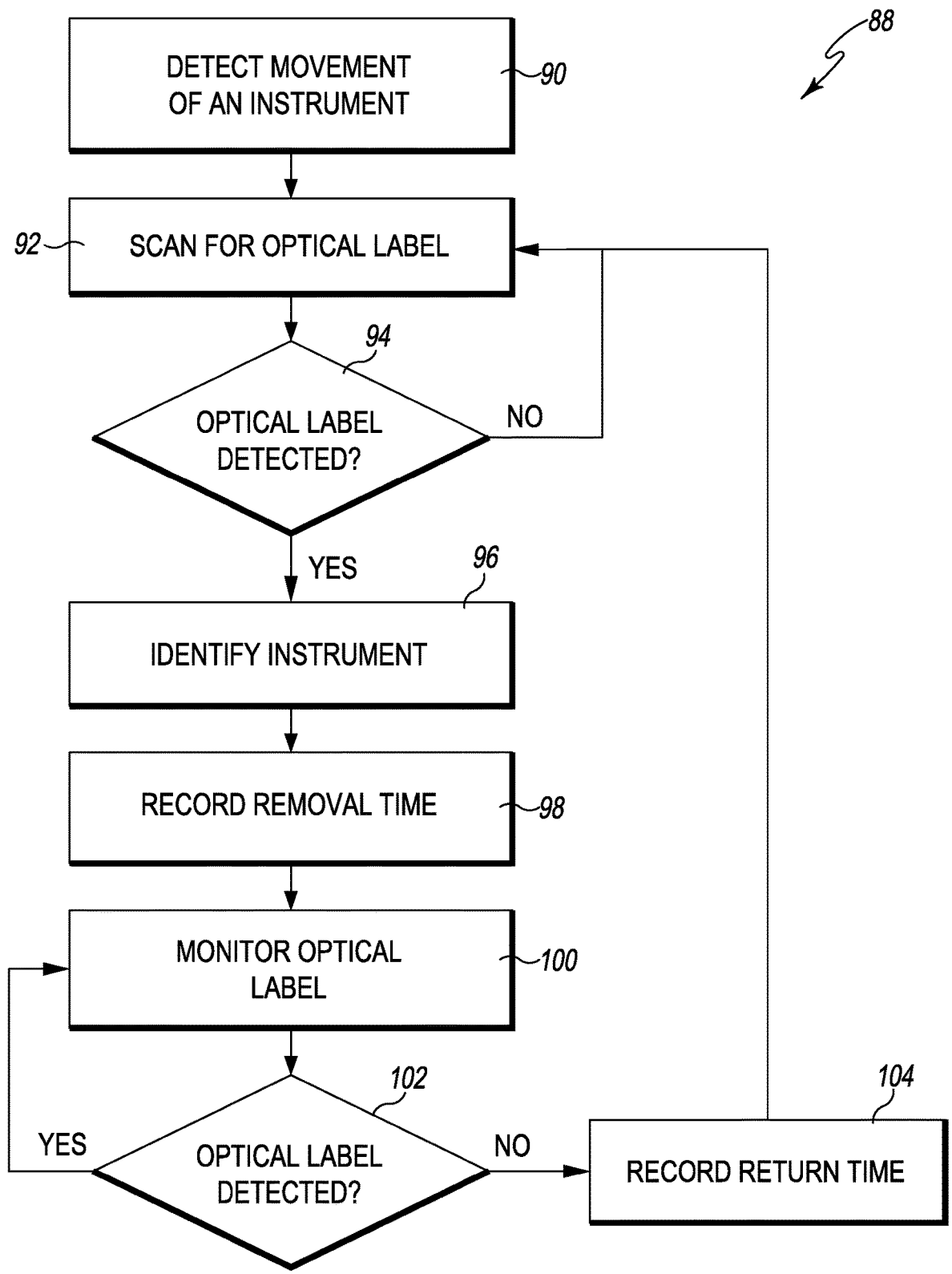
FIG. 4 is a flowchart of a routine for determining a duration of use of at least one of the plurality of orthopaedic surgical instruments of the orthopaedic surgical instrument system of FIG. 1.

FIG. 4 illustrates a flowchart for a routine 88 of operating the system 10. By way of example, the routine is described below with respect to removing the resection guide 30 from the instrument tray 12. It should be noted that the routine applies to any instrument 26 in the instrument tray 12. During operation, the instrument tray 12 is positioned in the operating room and is accessible to the surgeon or other users for use during the surgical procedure. The instruments 26 are positioned in the instrument tray 12 over their associated optical labels 28. The computing device 14 is positioned over the instruments 26 so that the imaging device 44 can view the optical labels 28 when the optical labels 28 are visible. At block 90, the motion sensor 76 detects movement of an instrument, e.g. the resection guide 30 being removed from the instrument tray 12.

Upon detecting movement, the motion sensor 76 sends an output signal to the processor 60 indicative of the motion. Based on the output signal from the motion sensor 76, the processor 60 activates the imaging device 44, at block 92. It should be noted that in an embodiment wherein the motion sensor 76 is turned off or not included in the computing device 14, the imaging device 44 is activated prior to the surgical procedure and continually scans for optical labels 28 throughout the procedure. While scanning for optical labels 28, the imaging device 44 sends output signals to the processor 60 indicating whether an optical label 28 is detected, at block 94. At the beginning of the surgical procedure, the optical labels 28, positioned under the instruments 26, are not readable by the imaging device 44. If the imaging device 44 cannot view an optical label 28, the processor 60 instructs the imaging device 44 to continue scanning for optical labels 28, at block 92. When resection guide 30 is removed from the instrument tray 12, the optical label 34 becomes visible and readable to the imaging device 44 causing the imaging device 44 to send an output signal to the processor 60. Based on the output signal from the imaging device 44, the processor 60 interprets the optical label 34 to identify the resection guide 30, at block 96.

After identifying the resection guide 30, the processor 60 records a removal time indicating the time that the resection guide 30 was removed, at block 98. At block 100, the processor 60 continues to receive output signals related to the optical label 34 from the imaging device 44. The processor 60 determines whether the optical label 34 is detected, at block 102. If the optical label 34 is still detected, the processor 60 continues to receive output signals related to the optical label 34 from the imaging device 44, at block 100. When the resection guide 30 is returned to the instrument tray 12, the optical label 34 is no longer readable and becomes undetected because the optical label 34 is covered by the resection guide 30. Based on an output signal from the imaging device 44, the processor 60 determines that the optical label 34 is undetected and, therefore, the resection guide 30 has been returned to the instrument tray 12. At block 104, the processor 60 records a return time that the resection guide 30 was returned to the instrument tray 12. The processor 60 then compares the return time to the removal time to determine a duration of use of the resection guide 30.

Although the above-routine is described in relation to detecting a single instrument 26, the processor 60 is capable of detecting multiple optical labels 28 simultaneously. For example, if the cutting guide 32 is also in use at the same time as the resection guide 30, the imaging device 44 is capable of sending output signals related to both the optical label 34 and the optical label 36. The processor 60 can record a removal time and return time of both the resection guide 30 and the cutting guide 32 so that a duration of use of both the resection guide 30 and the cutting guide 32 can be determined. Even if one of the resection guide 30 or the cutting guide 32 is returned to the instrument tray 12, the processor 60 can recognize that the other instrument 26 is still in use. Accordingly, the surgeon or other user may remove and return any number of instruments 26 at any time during the procedure, and the processor 60 will determine a duration of use that is specific to each instrument 26.

Data related to the duration of use of the instrument 26 is then stored in the data storage device 68. Alternatively, or in addition to, the data related to the duration of use is transmitted to the remote devices 72 over the network 74. After the surgical procedure, the surgeon or other hospital personnel can review the data related to the duration of use to determine which instruments 26 the surgeon had used during the procedure and for how long each instrument 26 was used.

Figure 5:
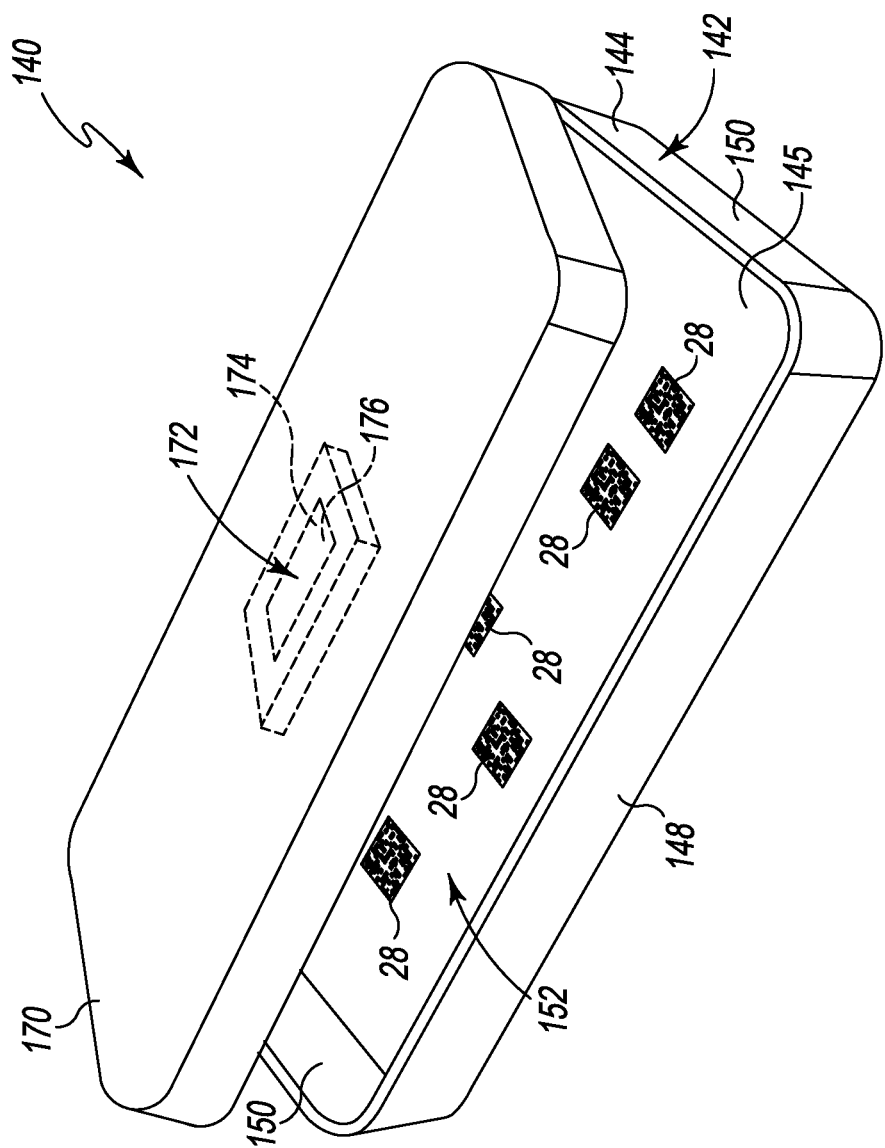
FIG. 5 is a front perspective view of another embodiment of an orthopaedic surgical instrument system.

Referring to FIG. 5, another embodiment of an orthopaedic surgical instrument system 140 includes an instrument tray 142 and the computing device 14. The instrument tray 142 includes a body 144 having a bottom wall 146 and a pair of spaced apart longitudinal walls 148 extending upwardly from the bottom wall 146. A pair of spaced apart end walls 150 extends upwardly from the bottom wall 146 between the longitudinal walls 148. The bottom wall 146, the longitudinal walls 148, and the end walls 150 cooperate to define a storage chamber 152 that houses the plurality of orthopaedic surgical instruments 26. The plurality of machine-readable optical labels 28 is positioned on the bottom wall 146.

A lid 170 is hingedly attached to one of the longitudinal walls 148. The lid 170 is moveable between a closed position, wherein the instruments 26 are sealed within the storage chamber 152, and an open position, wherein the instruments 26 are accessible to the surgeon or other user. In the illustrative embodiment, the lid 170 is in the opened position and retained at an angle so that an inner surface 172 of the lid 170 faces the bottom wall 146 and the optical labels 28. A sleeve 174 having a transparent cover 176 is positioned on the inner surface 172 of the lid 170. The computing device 14 is configured to be positioned within the sleeve 174 such that the imaging device 44 faces through the transparent cover 176. The lid 170 is arranged so that, when the computing device 14 is positioned within the sleeve 174, the imaging device 44 can view the optical labels 28 to carry out the method set forth above with respect to FIG. 4.

It should be noted that although the above-description of FIGS. 1-5 is described with respect to reading optical labels 28 in an instrument tray 12, the optical labels 28 may also be applied to a surgical drape. Prior to the surgical procedure, the instruments 26 are positioned over the associated optical labels 28 on the surgical drape. The computing device 14 is then positioned over the surgical drape to monitor the optical labels 28 as described herein. Additionally, although the present disclosure is described with respect to an orthopaedic surgical procedure, the system 10 may be used with any surgical procedure.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

The invention claimed is:

1. An orthopaedic surgical instrument system, the system comprising:
an orthopaedic surgical instrument tray,
an orthopaedic surgical instrument configured to be positioned in the instrument tray,
a machine-readable optical label positioned in the instrument tray and associated with the instrument,
an imaging device operable to read the optical label, and
an electronic controller including (i) a processor operable to receive output signals from the imaging device and (ii) a memory device,
wherein the optical label is sized to be covered by the instrument when the instrument is positioned in the instrument tray, and
wherein the memory device includes a plurality of instructions that, when read by the processor, cause the processor to:
(i) detect, based on the output signals from the imaging device, the optical label when the instrument is removed from the instrument tray,
(ii) interpret the optical label to identify the instrument and record a first time indicating that the instrument is removed from the instrument tray,
(iii) record, based on the output signals from the imaging device, a second time when the optical label is no longer detected, and
(iv) compare the first time to the second time to determine a duration of use of the instrument.

2. The system of claim 1, further comprising:
a second orthopaedic surgical instrument, and
a second machine-readable optical label associated with the second orthopaedic surgical instrument,
wherein the memory device includes a plurality of instructions that, when read by the processor, cause the processor to detect, based on the output signals from the imaging device, the second optical label when the second instrument is removed from the instrument tray.

3. The system of claim 2, wherein the memory device includes a plurality of instructions that, when read by the processor, cause the processor to interpret the second optical label to identify the second instrument.

4. The system of claim 3, wherein the memory device includes a plurality of instructions that, when read by the processor, cause the processor to determine a second duration of use of the second instrument.

5. The system of claim 1, further comprising a motion sensor to detect movement of the instrument, wherein the processor is operable to receive the output signals from the motion sensor, wherein the memory device includes a plurality of instructions that, when read by the processor, cause the processor to:
detect, based on the output signals from the motion sensor, movement of the instrument, and
retrieve the output signals from the imaging device when movement of the instrument is detected.

6. The system of claim 1 further comprising a database that stores data related to the duration of use.

7. An orthopaedic surgical instrument system, the system comprising:
an orthopaedic surgical instrument,
a machine-readable optical label associated with the instrument,
an imaging device operable to read the optical label, and
an electronic controller including (i) a processor operable to receive output signals from the imaging device and (ii) a memory device,
wherein the memory device includes a plurality of instructions that, when read by the processor, cause the processor to:

(i) detect, based on the output signals from the imaging device, the optical label when the instrument is in use, (ii) interpret the optical label to identify the instrument and record a first time indicating that the instrument is in use, (iii) record, based on the output signals from the imaging device, a second time when the instrument is no longer in use, and (iv) compare the first time to the second time to determine a duration of use of the instrument, and wherein the instrument tray further includes a body and lid hinged to the body, wherein the chamber is formed in the body, and the imaging device is positioned in the lid, the lid configured to angle relative to the body so that the imaging device is angled toward the optical label.

8. The system of claim 7, further comprising an instrument tray having a chamber to store the instrument, wherein the optical label is positioned on a bottom wall of the chamber.

9. The system of claim 7, further comprising a sleeve attached to the lid and configured to receive the imaging device.

10. The system of claim 7, further comprising an arm configured to hold the imaging device over the optical label.

11. The system of claim 7, further comprising a motion sensor to detect movement of the instrument, wherein the processor is operable to receive output signals from the motion sensor, wherein the memory device includes a plurality of instructions that, when read by the processor, cause the processor to:

detect, based on the output signals from the motion sensor, movement of the instrument, and retrieve the output signals from the imaging device when movement of the instrument is detected.

12. A method of determining a duration of use of an orthopaedic surgical instrument, the method comprising:

detecting a machine-readable optical label associated with an orthopaedic surgical instrument when the instrument is in use, interpreting the optical label to identify the instrument when the instrument is in use, determining when the optical label is no longer detected, and determining a duration of use of the instrument based on when the optical label was detected, wherein when the instrument is not in use the instrument is positioned over the optical label such that the optical label is unreadable, the method further comprising detecting the optical label when the optical label becomes readable as the instrument is removed from the optical label.

13. The method of claim 12, further comprising continuing to monitor the optical label when the optical label is readable.

14. The method of claim 13, further comprising determining that the optical label is no longer detected when the instrument is positioned back over the optical label after use and the optical label becomes unreadable.

15. The method of claim 12, further comprising detecting a second optical label associated with a second instrument when the second instrument is in use.

16. The method of claim 15, further comprising:

interpreting the second optical label to identify the second instrument when the second instrument is in use, and determining a duration of use of the second instrument based on when the second optical label was detected.

17. The method of claim 12, wherein the optical label is positioned in an instrument tray, the method further comprising detecting the optical label when the instrument is removed from the instrument tray.

18. The method of claim 12, wherein the optical label is positioned on a surgical drape, the method further comprising detecting the optical label when the instrument is removed from the surgical drape.

* * * * *